(12) United States Patent
Blaeser et al.

(10) Patent No.: US 6,802,849 B2
(45) Date of Patent: Oct. 12, 2004

(54) STENT DELIVERY SYSTEM

(75) Inventors: David J Blaeser, Champlin, MN (US); Linda R. Lorentzen Cornelius, Wayzata, MN (US); Martin R. Willard, Maple Grove, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 10/153,276

(22) Filed: May 21, 2002

(65) Prior Publication Data

US 2002/0138081 A1 Sep. 26, 2002

Related U.S. Application Data

(63) Continuation of application No. 09/387,179, filed on Aug. 31, 1999, now Pat. No. 6,391,032, which is a continuation of application No. 08/917,074, filed on Aug. 22, 1997, now Pat. No. 5,944,726, which is a continuation-in-part of application No. 08/807,791, filed on Feb. 28, 1997, now Pat. No. 6,077,273, which is a continuation-in-part of application No. 08/702,150, filed on Aug. 23, 1996, now Pat. No. 6,007,543, which is a continuation-in-part of application No. 08/697,453, filed on Aug. 23, 1996, now abandoned.

(51) Int. Cl.[7] .............................................. A61F 11/00
(52) U.S. Cl. ...................... 606/191; 606/198; 606/108
(58) Field of Search ................................ 606/195, 198, 606/194, 108, 191; 604/96

(56) References Cited

U.S. PATENT DOCUMENTS

| | | |
|---|---|---|
| 2,690,595 A | 10/1954 | Raiche |
| 4,271,839 A | 6/1981 | Fogarty et al. |
| 4,327,736 A | 5/1982 | Inoue |
| 4,328,056 A | 5/1982 | Snooks |
| 4,338,942 A | 7/1982 | Fogarty |
| 4,403,612 A | 9/1983 | Fogarty |

(List continued on next page.)

FOREIGN PATENT DOCUMENTS

| | | |
|---|---|---|
| EP | 0 266 957 | 10/1987 |
| EP | 0 266 957 A2 | 5/1988 |
| EP | 0 274 411 A2 | 7/1988 |
| EP | 0 420 488 A1 | 4/1991 |
| EP | 0 442 657 A2 | 8/1991 |
| EP | 0 457 456 A1 | 11/1991 |
| EP | 0 529 039 A1 | 2/1993 |

(List continued on next page.)

OTHER PUBLICATIONS

Kim et al., Mechanical and Transport Properties of Coextruded Films, *Journal of Applied Polymer Science*, vol. 29, p. 2359–2382 (1984).

May et al., Polyvinyl and vinyl copolymers, *Modern Plastics Encyclopedia*, 1985–1987, p. 82.

Daniel O. Adams, BME, PTCA Balloon Materials, Their Characteristics and Impact on Catheter Selection, Sales training Technical Notes.

(List continued on next page.)

*Primary Examiner*—Jerome W. Donnelly
(74) *Attorney, Agent, or Firm*—Vidas, Arrett & Steinkraus PA

(57) ABSTRACT

A stent delivery system to facilitate introduction and placement of a stent, including a catheter having an expandable distal portion constructed and arranged for expanding the outer diameter of the catheter from a contracted state to an expanded state: a stent positioned around the distal portion of the catheter having a contracted condition and being expandable to an expanded condition, and being sized in the contracted condition to closely surround the catheter in the contracted state, the expandable distal portion of the catheter including a balloon within which there is included on the catheter shaft at least one body of a diameter larger than the catheter shaft to which the stent and balloon are fitted, as by crimping, for holding the stent in place until it is released therefrom by expansion of the balloon and further including axially slidable sleeves over the stent in the unexpanded condition.

11 Claims, 3 Drawing Sheets

U.S. PATENT DOCUMENTS

| | | | |
|---|---|---|---|
| 4,423,725 A | 1/1984 | Baran et al. | |
| 4,576,871 A | 3/1986 | Oestreich | |
| 4,608,984 A | 9/1986 | Fogarty | |
| 4,637,396 A | 1/1987 | Cook | |
| 4,649,914 A | 3/1987 | Kowalewski | |
| 4,702,252 A | 10/1987 | Brooks et al. | |
| 4,733,665 A | 3/1988 | Palmaz | |
| 4,735,665 A | 4/1988 | Miyauchi et al. | |
| 4,740,207 A | 4/1988 | Kreamer | |
| 4,744,366 A | 5/1988 | Jang | |
| 4,763,654 A | 8/1988 | Jang | |
| 4,787,388 A | 11/1988 | Hofmann | |
| 4,848,343 A | 7/1989 | Wallsten et al. | |
| 4,875,480 A | 10/1989 | Imbert | |
| 4,885,194 A | 12/1989 | Tight, Jr. et al. | |
| 4,932,958 A | 6/1990 | Reddy et al. | |
| 4,950,227 A * | 8/1990 | Savin et al. | 606/192 |
| 4,983,167 A | 1/1991 | Sahota | |
| 4,990,139 A | 2/1991 | Jang | |
| 4,994,033 A | 2/1991 | Shockey et al. | |
| 5,007,926 A | 4/1991 | Derbyshire | |
| 5,026,377 A | 6/1991 | Burton et al. | |
| 5,037,392 A | 8/1991 | Hillstead | |
| 5,049,131 A | 9/1991 | Deuss | |
| 5,049,132 A | 9/1991 | Shaffer et al. | |
| 5,057,092 A | 10/1991 | Webster, Jr. | |
| 5,071,406 A | 12/1991 | Jang | |
| 5,071,407 A | 12/1991 | Termin et al. | |
| 5,090,958 A | 2/1992 | Sahota | |
| 5,096,848 A | 3/1992 | Kawamura | |
| 5,108,370 A | 4/1992 | Walinsky | |
| 5,108,416 A * | 4/1992 | Ryan et al. | 606/194 |
| 5,116,318 A * | 5/1992 | Hillstead | 604/96 |
| 5,158,548 A | 10/1992 | Lau et al. | |
| 5,192,295 A * | 3/1993 | Danforth et al. | 606/194 |
| 5,195,969 A | 3/1993 | Wang et al. | |
| 5,226,880 A | 7/1993 | Martin | |
| 5,226,889 A | 7/1993 | Sheiban | |
| 5,242,399 A | 9/1993 | Lau et al. | |
| 5,264,260 A | 11/1993 | Saab | |
| 5,270,086 A | 12/1993 | Hamlin | |
| 4,733,665 A | 1/1994 | Palmaz | |
| 5,290,306 A | 3/1994 | Trotta et al. | |
| 5,295,962 A | 3/1994 | Crocker et al. | |
| 5,298,300 A | 3/1994 | Hosoi et al. | |
| 5,304,132 A | 4/1994 | Jang | |
| 5,304,198 A * | 4/1994 | Samson | 606/194 |
| 5,306,250 A | 4/1994 | March et al. | |
| 5,342,305 A | 8/1994 | Shonk | |
| 5,344,401 A | 9/1994 | Radisch et al. | |
| 5,344,402 A | 9/1994 | Crocker | |
| 5,344,426 A | 9/1994 | Lau et al. | |
| 5,348,538 A | 9/1994 | Wang et al. | |
| 5,358,487 A | 10/1994 | Miller | |
| 5,378,237 A | 1/1995 | Boussignac et al. | |
| 5,403,341 A * | 4/1995 | Solar | 606/198 |
| 5,405,380 A | 4/1995 | Gianotti et al. | |
| 5,409,495 A * | 4/1995 | Osborn | 606/108 |
| 5,415,635 A | 5/1995 | Bagaoisan et al. | |
| 5,415,664 A | 5/1995 | Pinchuk | |
| 5,441,515 A * | 8/1995 | Khosravi et al. | 606/194 |
| 5,445,646 A * | 8/1995 | Euteneuer et al. | 606/198 |
| 5,447,497 A | 9/1995 | Sogard et al. | |
| 5,453,090 A | 9/1995 | Martinez et al. | |
| 5,458,615 A | 10/1995 | Klemm et al. | |
| 5,470,313 A | 11/1995 | Crocker et al. | |
| 5,478,320 A | 12/1995 | Trotta | |
| 5,490,839 A | 2/1996 | Wang et al. | |
| 5,507,768 A | 4/1996 | Lau et al. | |
| 5,512,051 A | 4/1996 | Wang et al. | |
| 5,534,007 A | 7/1996 | St. Germain et al. | |
| 5,536,252 A | 7/1996 | Imran et al. | |
| 5,545,209 A * | 8/1996 | Roberts et al. | 606/108 |
| 5,571,086 A * | 11/1996 | Kaplan et al. | 604/96 |
| 5,587,125 A | 12/1996 | Roychowdhury | |
| 5,591,222 A * | 1/1997 | Susawa et al. | 606/195 |
| 5,591,228 A * | 1/1997 | Edoga | 606/194 |
| 5,632,760 A * | 5/1997 | Sheiban et al. | 606/195 |
| 5,643,278 A * | 7/1997 | Wijay | 606/108 |
| 5,653,691 A * | 8/1997 | Rupp et al. | 604/96 |
| 5,695,498 A * | 12/1997 | Tower | 606/108 |
| 5,817,102 A | 10/1998 | Johnson et al. | 606/108 |

FOREIGN PATENT DOCUMENTS

| | | |
|---|---|---|
| EP | 0 420 488 B1 | 4/1993 |
| EP | 0 540 858 | 5/1993 |
| EP | 0 257 091 B1 | 7/1993 |
| EP | 0 553 960 A1 | 8/1993 |
| EP | 0 274 846 B1 | 2/1994 |
| EP | 0 582 870 A2 | 2/1994 |
| EP | 0 627 201 A1 | 12/1994 |
| EP | 0 699 451 A2 | 3/1996 |
| EP | 0 707 837 A1 | 4/1996 |
| WO | WO 92/08512 | 5/1992 |
| WO | WO 92/19440 | 11/1992 |
| WO | WO 93/19703 | 10/1993 |
| WO | WO 95/09667 | 4/1995 |
| WO | WO 95/22367 | 8/1995 |
| WO | WO 96/03072 | 2/1996 |
| WO | WO96/03072 A1 | 2/1996 |
| WO | WO 96/03092 A1 | 2/1996 |
| WO | WO96/03092 A1 | 2/1996 |
| WO | WO 96/04951 | 2/1999 |

OTHER PUBLICATIONS

Julio C. Palmaz et al., *Expandable Intraluminal Graft: A Preliminary Study, Work in Progress*, From the Departments of Radiology (J.C.P., R.R.S., S. R.R.) and Pathology (F.O.T.) University of Texas Health Science Center at Sanantonio and Memorial Medical Center (W.J.K.), Corpus Christi, Texas. *RADIOLOGY.* vol. 356, No. 1, pp. 73–77.

Tailoring Expansion Properties of Balloons for Medical Devices, *HealthWatch*, Prepared Oct. 25, 1994 at 3:04, p. 3.

Avanindra Jain et al., Effect of Inflation Pressures on Coronary Angioplasty Balloons, *The American Journal of Cardiology*, Jan. 1, 1986. vol. 57, p. 26–28.

Dialog Patent Search dated Nov. 3, 1994.

Julio C. Palmaz et al., 156 *RADIOLOGY* 73 (1985), *Expandable Intraluminal Graft: A Preliminary Study.*

Julio C. Palmaz et al., *Expandable Intraluminal Graft: A Preliminary Study work in progress*, RADIOLOGY 1985; 156:73–77.

* cited by examiner

STENT DELIVERY SYSTEM

This application is a continuation of U.S. application Ser. No. 09/387,179, filed Aug. 31, 1999, now U.S. Pat. No. 6,391,032, which is a continuation of U.S. application Ser. No. 08/917,074, filed Aug. 22, 1997, now U.S. Pat. No. 5,944,726, which is a Continuation-In-Part application based on U.S. Ser. No. 08/807,791 filed Feb. 28, 1997, now U.S. Pat. No. 6,077,273, issued Jun. 20, 2000, entitled CATHETER SUPPORT FOR STENT DELIVERY which is a Continuation-In-Part based on U.S. Ser. No. 08/702,150 filed Aug. 23, 1996, now U.S. Pat. No. 6,007,543, issued Dec. 28, 1999, entitled STENT DELIVERY SYSTEM and U.S. Ser. No. 08/697,453 filed Aug. 23, 1996, now abandoned, entitled PRE-MOUNTED STENT DELIVERY DEVICE WITH INFLATABLE TUBE COMPONENT, all of which are incorporated by reference in their entirety.

BACKGROUND OF THE INVENTION

In typical PTCA procedures, a guiding catheter is percutaneously introduced into the cardiovascular system of a patient through a vessel and advanced through therein until the distal end thereof is at a desired location in the vasculature. A guidewire and a dilatation catheter having a balloon on the distal end thereof are introduced through the guiding catheter with the guidewire sliding through the dilatation catheter. The guidewire is first advanced out of the guiding catheter into the patient's coronary vasculature and the dilatation catheter is advanced over the previously advanced guidewire until the dilatation balloon is properly positioned across the lesion. Once in position across the lesion, the flexible, expandable, preformed balloon is inflated to a predetermined size with a liquid or gas at relatively high pressures, such as greater than about four atmospheres, to radially compress the arthrosclerotic plaque of the lesion against the inside of the artery wall and thereby dilate the lumen of the artery. The balloon is then deflated to a small profile so that the dilatation catheter may be withdrawn from the patients vasculature and blood flow resumed through the dilated artery.

In angioplasty procedures of the kind described above, there may be restenosis of the artery, which either necessitates another angioplasty procedure, a surgical by-pass operation, or some method of repairing or strengthening the area. To help prevent restenosis and strengthen the area, a physician can implant an intravascular prosthesis for maintaining vascular patency, called a stent, inside the artery at the lesion. The stent is expanded to a larger diameter for placement in the vasculature, often by the balloon portion of the catheter. Stents delivered to a restricted coronary artery, expanded to a larger diameter as by a balloon catheter, and left in place in the artery at the site of a dilated lesion are shown in U.S. Pat. No. 4,740,207 to Kreamer; U.S. Pat. No. 5,007,926 to Derbyshire; U.S. Pat. No. 4,733,665 to Palmaz; U.S. Pat. No. 5,026,377 to Burton et al.; U.S. Pat. No. 5,158,548 to Lau et al.; U.S. Pat. No. 5,242,399 to Lau et al.; U.S. Pat. No. 5,344,426 to Lau et al.; U.S. Pat. No. 5,415,664 to Pinchuk; U.S. Pat. No. 5,453,090 to Martinez et al.; U.S. Pat. No. 4,950,227 to Savin; U.S. Pat. No. 5,403,341 to Solar; U.S. Pat. No. 5,108,416 to Ryan et al. and European Patent Application No. 707 837 A1 to Sheiban, all of which are incorporated herein by reference. A stent particularly preferred for use with this invention is described in PCT Application No. 960 3092 A1, published Feb. 8, 1996, the content of which is also incorporated herein by reference.

The present invention is particularly directed to improved arrangements for releasably attaching the stent to the catheter to facilitate delivery thereof. Releasable sleeves are shown in U.S. Pat. No. 4,950,227 to Savin. This patent is incorporated herein by reference.

SUMMARY OF THE INVENTION

This invention concerns apparatus suitable for delivery of stents to body cavities. In general, stents are prosthetic devices which can be positioned within a body cavity, for example, a blood vessel of the body of a living human or in some other difficultly accessible place. The stent prosthesis is formed of a generally tubular body, the diameter of which can be decreased or increased. Stents are particularly useful for permanently widening a vessel which is either in a narrowed state, or internally supporting a vessel damaged by an aneurysm. Such stents are typically introduced into the body cavity by use of a catheter. The catheter is usually of the balloon catheter type in which the balloon is utilized to expand the stent, which is positioned over the balloon, to place it in a selected location in the body cavity. The present invention is particularly directed to improved arrangements for releasably attaching the stent to the catheter to facilitate delivery thereof. The stent is held in place on the catheter by means of an enlarged body carried by the catheter shaft within the balloon to which the stent and balloon are fitted, as by crimping in combination with one or more sleeves releaseably overlying an end portion or portions of a stent and balloon.

DESCRIPTION OF THE PREFERRED EMBODIMENTS

Figure 1:
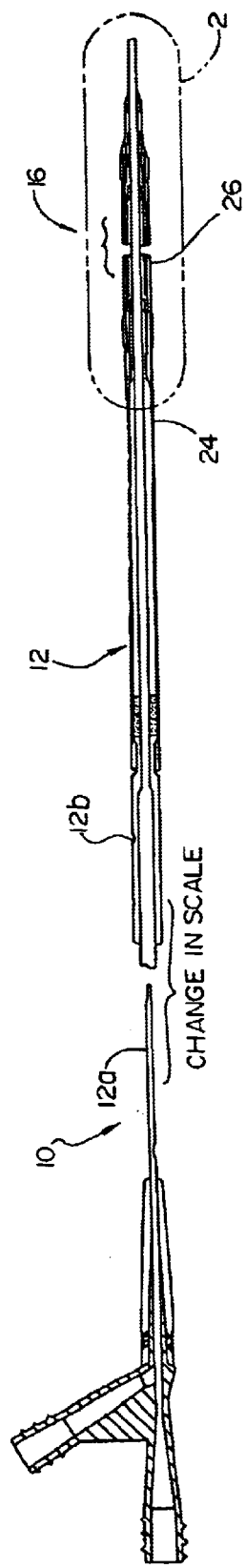
FIG. 1 is an isometric view, a portion of which is enlarged and in longitudinal section, of a balloon catheter having a stent fixed to the catheter over the balloon.
Figure 2:
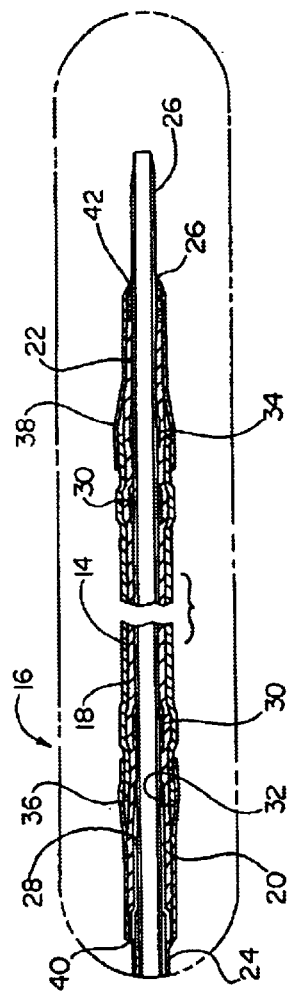
FIG. 2 is an even more enlarged view in longitudinal cross-section of the distal end portion of the catheter of FIG. 1.

Referring to FIGS. 1 and 2 a stent delivery system generally indicated at 10 includes a balloon catheter 12 having a balloon 14 on a distal end portion generally indicated at 16. FIG. 1 shows a proximal portion of the catheter at 12a and a distal portion 12b in enlarged view. FIG. 2 shows the distal end portion 16 in an even more enlarged view. The illustrative catheter 12 is of the type known as an over the wire catheter. However, other types of catheters may be used, such as rapid exchange/single operator and fixed wire types. The balloon 14 is fixed to the catheter 12 by standard means. The balloon is shown in its contracted state in FIGS. 1 and 2. A stent 18 is fixed about the balloon by crimping it thereto. The stent has a larger expanded diameter which is obtained when the balloon is expanded in the known manner. That is, the stent is released from the catheter upon expansion of the balloon when placed in a vessel. When the balloon is then deflated, removal of the balloon and catheter may be accomplished while leaving the stent in place.

As is known in the art the balloon is either bonded at its ends by adhesive 20 and 22, respectively to the outer member 24 of the catheter and to the inner member 26 of the catheter in the manner as shown, or is made one-piece with the outer member as is known in the art. The catheter balloon may be inflated by fluid (gas or liquid) from an inflation port extending from a lumen 28 contained in the catheter shaft and opening into the balloon as shown, or by other known arrangements, depending on the design of the catheter. The details and mechanics of balloon inflation and specific overall catheter construction will vary according to the particular design involved in any given instance, and are known in the art per se. All variations are acceptable for use with this invention.

Any balloon expandable stent may be used with this invention. Many are known in the art including plastic and metal stents. Some are more well known such as the stainless steel stent shown in U.S. Pat. No. 4,735,665; the wire stent shown in U.S. Pat. No. 4,950,227; another metal stent shown in European Patent Application No. EPO 707 837 A1 and that shown in U.S. Pat. No. 5,445,646. All of these patents are incorporated herein by reference. Also, shape memory metal stents may be used. As already indicated the stent of PCT Application No. 960 3092 A1 is particularly preferred.

The stent is typically about 16 mm long, while the balloon may be 20 mm long. These dimensions, however, are merely representative for illustrative purposes only and are not meant to be limiting. The stent is positioned over the balloon portion of the dilatation catheter and gently crimped onto the balloon either by hand or with a tool such as a pliers or the like to be mounted for delivery as shown in FIGS. 1 and 2. The crimping may be accomplished by either the manufacturer or the physician.

In accordance with one embodiment of this invention, a mounting bodies 30, seen in FIGS. 1 and 2 are included inside balloon 14 to provide a cushion and/or substrate of enlarged diameter relative to the shaft to support and hold the stent and secure it during crimping and the delivery procedure. The mounting bodies are preferably located in the body portion of the balloon.

In the embodiment shown, mounting bodies 30 are ring-like in form and inner lumen 26, providing an enlarged area or portion for receiving the balloon and stent when the latter is crimped. Marker bands 32 and 34 may also be included on inner 26 as shown. Any radiopaque material such as gold is useful for this purpose. Although, the material of the mounting bodies may be hard, it is preferably of any thermoplastic elastomer having elastic or deformable properties, more preferably of a relatively resilient elastomer material, e.g., silicone, preferably a lower durometer silicone or polyurethane, such as Tecothane 1055D. A deformable thermoplastic material such as high density polyethylene (HDPE) may be used. Any deformation of resilient material of the mounting body when the stent/balloon is crimped to it causes a radial outward force on the stent/balloon increasing the friction therebetween despite a recoil of the stent.

The stent is also fixed in position by two overlying retaining sleeves 36 and 38. Sleeves 36 and 38 are formed of polyurethane, preferably Tecothane 1055D, and are axially fixed on catheter 12 by adhesive plugs 40 and 42 of urethane adhesive. The plugs of adhesive may be tapered to the catheter as shown to facilitate movement of the catheter in a vessel. The sleeves overlap the marginal end portions of stent 18 as shown.

A lubricating solution such as silicone fluid may be used between balloon 14 and sleeves 36 and 38 and thereon to facilitate release of stent 18 from the sleeves.

Figure 3:
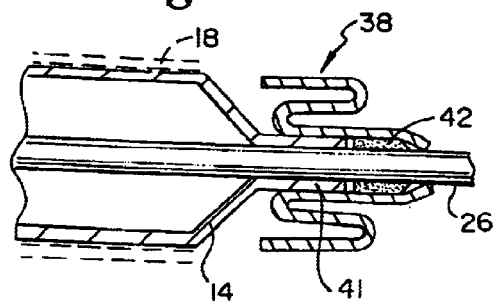
FIG. 3 is a schematic showing of one form of retraction of the releasable sleeve upon expansion of the balloon.
Figure 4:
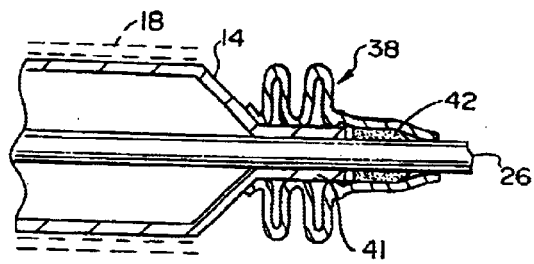
FIG. 4 is a schematic showing of another form of retraction of the releasable sleeve upon expansion of the balloon.
Figure 5:
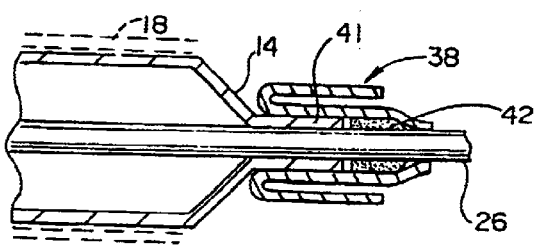
FIG. 5 is yet another form of retraction of the releasable sleeve upon expansion of the balloon.
Figure 6:
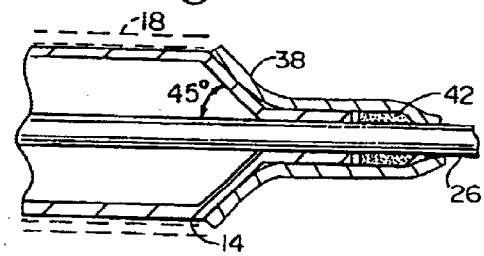
FIG. 6 is a schematic showing of yet another form of retraction of the releasable sleeve upon expansion of the balloon.

During delivery, the balloon catheter is advanced through and positioned in a patient's vasculature so that the stent is adjacent to the portion of the vessel where treatment is to take place. The balloon is inflated to expand the stent to an enlarged diameter. At this time, expansion of the balloon causes the end margin of the sleeves to slide axially from over the stent thereby releasing the ends of the stent from the catheter. Various forms of retraction of sleeves 36 and 38 are shown in FIGS. 3–6. These figures illustrate the configuration of the sleeves 36 and 38 in their retracted state after the balloon 14 has been fully expanded. Only the distal sleeve 38 is shown. FIG. 3 illustrates the preferably retraction configuration. To promote easier retraction sleeves are coated with silicone. The sleeves are preferably adhered to the outer shaft 24 and the inner shaft 26 at point 40 (not shown), 42, but may be adhered further up the waste 41 of the balloon. The retraction configurations may be controlled by either pre-creasing the sleeves or adhering the sleeve to a point further up on the waist of the balloon. The sleeves have a tendency of folding at a pre-fold crease or at the point of adherence. A preferred cone angle of 45° for the balloon is shown in FIG. 6, which shows an expanded balloon 14 and retracted sleeves 36,38. When the stent has reached the desired diameter, the balloon is deflated so that the catheter may be removed leaving the stent in place.

Figure 7:
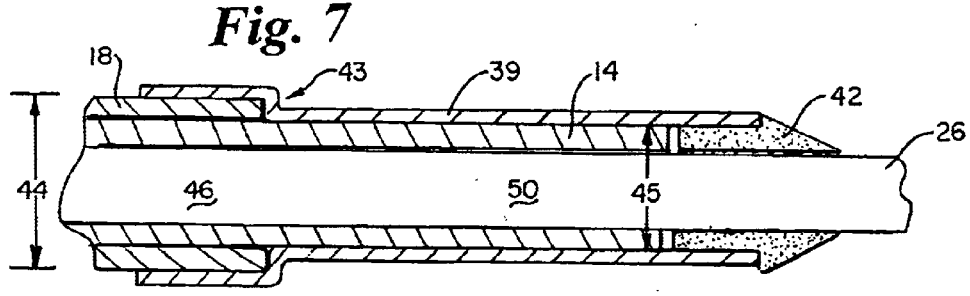
FIG. 7 is a schematic showing of a modified shape for the releasable sleeve.

A modified sleeve 39 configuration is shown in FIG. 7 in stepped form 43 having a large diameter at 44 in one section 46 and a small diameter 45 in a second section 50.

Figure 8:
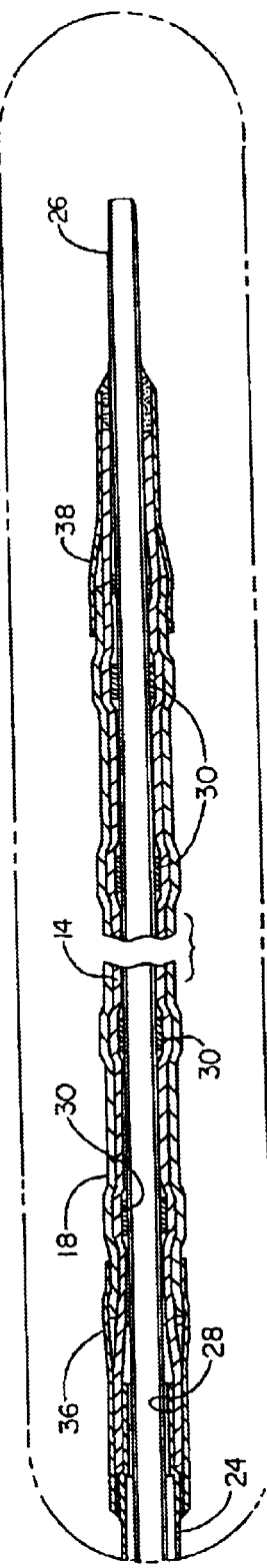
FIG. 8 is a schematic showing in cross-section of another embodiment of the invention with a stent not yet mounted.
Figure 9:
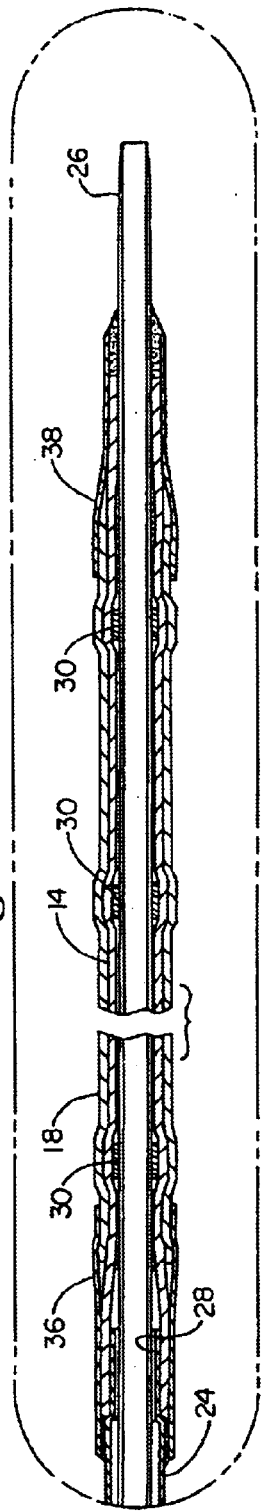
FIG. 9 is a schematic showing of another embodiment of the invention.
Figure 10:
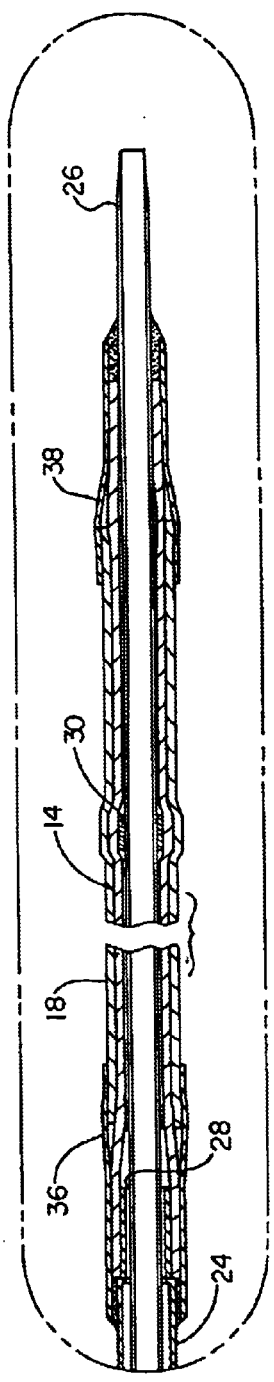
FIG. 10 is a schematic showing of yet another embodiment of the invention.

FIGS. 8–10 show alternative embodiments of the invention. Specifically, alternative positioning and number of mounting bodies 30. These figures show an unexpanded balloon having the mounted bodies 30 within the balloon. They are meant to illustrate essentially the same structure as shown in FIG. 2 differing only in the number and positioning of the mounted bodies 30. In the embodiment shown in FIG. 8, the ring-like mounting body 30 is singular. Another similar version is shown in FIG. 9 which includes three ring-like mounting bodies 30. The embodiment shown in FIG. 10 includes four ring-like mounting bodies 30.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. A stent delivery system comprising in combination:
a catheter having a distal region and an inner shaft;
an expandable balloon mounted on and about the catheter at the distal region, said expandable balloon having an expanded state, a collapsed state, a first waist, a second waist, a first cone portion, a second cone portion and a body portion, wherein the cone portions are between the body portion and the waists, respectively and wherein the first waist and the second waist are secured to the catheter;

an expandable stent mounted on and about the expandable balloon, the expandable stent having a first end, a second end, a collapsed state and an expanded state;

at least one stent retaining sleeve, said at least one stent retaining sleeve having a length and a resting diameter, wherein the resting diameter is substantially constant along its length, a first end portion and a second end portion, wherein the second end portion covers the first end of the expandable stent, the at least one stent retaining sleeve having a region which is pre-creased, such that, when the expandable balloon expands, the at least one stent retaining sleeve folds onto itself at the region which is pre-creased.

2. The stent delivery system of claim 1, wherein the at least one stent retaining sleeve folds inwardly relative to the catheter distal region when the expandable balloon is expanded.

3. The stent delivery system of claim 1, wherein the at least one stent retaining sleeve folds outwardly relative to the catheter distal region when the expandable balloon is expanded.

4. The stent delivery system of claim 1, wherein the at least one stent retaining sleeve has at least two pre-creases, wherein the at least one stent retaining sleeve folds at the at least two pre-creases when the expandable balloon is expanded.

5. The stent delivery system of claim 1, wherein the at least one stent retaining sleeve has three pre-creases, wherein the at least one stent retaining sleeve has three folds when the expandable balloon is expanded.

6. The stent delivery system of claim 1, wherein the pre-crease is circumferential.

7. A stent delivery system comprising in combination:

a catheter having a distal region and an inner shaft;

an expandable balloon mounted on and about the catheter at the distal region, said expandable balloon having an expanded state, a collapsed state, a first waist, a second waist, a first cone portion, a second cone portion and a body portion, wherein the cone portions are between the body portion and the waists, respectively and wherein the first waist and the second waist are secured to the catheter;

an expandable stent mounted on and about the expandable balloon, the expandable stent having a first end, a second end, a collapsed state and an expanded state;

at least one stent retaining sleeve, said at least one stent retaining sleeve having a length, a first end portion and a second end portion, wherein the second end portion covers the first end of the expandable stent, the at least one stent retaining sleeve having a first portion having a first resting diameter, a second portion having a second resting diameter and a step formed between the first portion and the second portion, wherein the second resting diameter is greater than the first resting diameter and wherein the second end portion of the at least one stent retaining sleeve is part of the second portion of the at least one stent retaining sleeve and wherein, when the expandable balloon is in its collapsed state, the at least one stent retaining sleeve is in contact with the expandable balloon along the sleeve's length where the at least one stent retaining sleeve is radially adjacent to the expandable balloon.

8. The stent delivery system of claim 7, wherein the step is positioned directly adjacent to and hugs the first end of the expandable stent.

9. The stent delivery system of claim 7, wherein the first portion of the at least one stent retaining sleeve is bonded to at least a portion of the first waist of the expandable balloon.

10. The stent delivery system of claim 9, the first portion of the at least one stent retaining sleeve having an axial length, wherein the first portion of the at least one stent retaining sleeve is bonded to the first waist of the expandable balloon substantially along the axial length of the first portion of the at least one stent retaining sleeve.

11. The stent delivery system of claim 1, wherein, when the at least one stent retaining sleeve folds onto itself at the region which is pre-creased, it forms an acute angle extending from the pre-creased region.

* * * * *